(12) United States Patent
    Fabrigas

(10) Patent No.:     US 12,661,472 B2
(45) Date of Patent:        Jun. 23, 2026

(54) NECK-MOUNT POWERED RESPIRATOR

(71) Applicant: F3 BIODESIGNS, LLC, San Antonio, TX (US)

(72) Inventor: Francis Palma Fabrigas, San Antonio, TX (US)

(73) Assignee: F3 BIODESIGNS, LLC, San Antonio, TX (US)

( * ) Notice: Subject to any disclaimer, the term of this patent is extended or adjusted under 35 U.S.C. 154(b) by 824 days.

(21) Appl. No.: 18/098,738

(22) Filed: Jan. 19, 2023

(65) Prior Publication Data

US 2023/0233789 A1     Jul. 27, 2023

Related U.S. Application Data

(60) Provisional application No. 63/302,516, filed on Jan. 24, 2022.

(51) Int. Cl.
    *A62B 9/04*        (2006.01)
    *A61M 16/06*        (2006.01)
    (Continued)

(52) U.S. Cl.
    CPC ........... *A61M 16/0683* (2013.01); *A62B 7/10* (2013.01); *A62B 9/04* (2013.01); *A62B 18/045* (2013.01)

(58) Field of Classification Search
    CPC .. A62B 7/10; A62B 9/04; A62B 17/04; A62B 18/003; A62B 18/006; A62B 18/02;
    (Continued)

(56) References Cited

U.S. PATENT DOCUMENTS

| | | |
|---|---|---|
| 8,230,852 B2 | 7/2012 | Zhang et al. |
| 9,095,803 B2 | 8/2015 | Augustine et al. |
| | (Continued) | |

FOREIGN PATENT DOCUMENTS

| | | |
|---|---|---|
| EP | 3159045 B1 | 8/2021 |
| EP | 3226981 B1 | 8/2022 |
| | (Continued) | |

OTHER PUBLICATIONS

English Machine Translation of KR-102035977-B1 provided by PE2E (Year: 2019).*

(Continued)

*Primary Examiner* — Joseph D. Boecker
*Assistant Examiner* — Brian T Khong
(74) *Attorney, Agent, or Firm* — H. Brock Kolls

(57)        ABSTRACT

The present invention relates to neck-mount powered respirators and methods of use. The respirators comprise an air handler, a temple rail, and a shoulder rail that fits around the back of the neck and over the shoulders of the wearer. The air handler is either positioned behind the neck of the wearer or integrated into a hollow shoulder rail. The temple rail is hollow and sized to fit snugly around the back of the head and contact with the temples of the wearer. A neck conduit is hollow and interconnects the shoulder rail and the temple rail forming an airflow channel. A face shield includes an elastic band that covers the temple rail temple vents, and the eyes, nose, and mouth of the wearer. Purified filtered air inflates the region between the face shield and the face of the wearer allowing the wearer to breathe the purified filtered air.

20 Claims, 12 Drawing Sheets

(51) Int. Cl.
 *A62B 7/10*          (2006.01)
 *A62B 18/04*         (2006.01)

(58) Field of Classification Search
 CPC ..... A62B 18/04; A62B 18/045; A62B 18/084;
  A41D 13/1161; A41D 13/1184; A41D
  13/1192; A41D 13/0025
 See application file for complete search history.

(56) References Cited

U.S. PATENT DOCUMENTS

| | | | |
|---|---|---|---|
| 10,537,754 B1 | 1/2020 | Vukelja | |
| 11,187,241 B1 | 11/2021 | Liu et al. | |
| 2007/0163586 A1* | 7/2007 | Burnett | A62B 23/02 |
| | | | 128/205.29 |
| 2010/0108067 A1* | 5/2010 | Walker | A62B 18/04 |
| | | | 128/205.24 |
| 2010/0198322 A1 | 8/2010 | Joseph et al. | |
| 2011/0289954 A1* | 12/2011 | Zhang | A62B 18/003 |
| | | | 62/426 |
| 2015/0375019 A1 | 12/2015 | VanDerWoude et al. | |
| 2017/0000359 A1 | 1/2017 | Kohli et al. | |
| 2018/0035741 A1 | 2/2018 | VanDerWoude et al. | |

| | | | | |
|---|---|---|---|---|
| 2018/0084848 A1* | 3/2018 | Pavalarajan | | H03M 5/145 |
| 2018/0296864 A1 | 10/2018 | Feasey et al. | | |
| 2018/0311515 A1 | 11/2018 | Wilson et al. | | |
| 2020/0187574 A1 | 6/2020 | Te Hsiang | | |
| 2020/0406069 A1 | 12/2020 | Fu | | |
| 2022/0062668 A1 | 3/2022 | Piatt | | |
| 2022/0080227 A1 | 3/2022 | Cohen et al. | | |
| 2022/0106963 A1 | 4/2022 | Li | | |

FOREIGN PATENT DOCUMENTS

| | | | | | | |
|---|---|---|---|---|---|---|
| KR | 20170127845 A | * | 11/2017 | .......... | A62B 18/006 |
| KR | 102035977 B1 | * | 10/2019 | ............ | A62B 23/02 |
| KR | 20210145046 A | * | 12/2021 | .............. | A62B 7/12 |
| WO | 2021142982 A1 | | 7/2021 | | |
| WO | 2021143888 A1 | | 7/2021 | | |
| WO | 2022128771 A1 | | 6/2022 | | |

OTHER PUBLICATIONS

English Machine Translation of KR-20170127845-A provided by PE2E (Year: 2017).*
English Machine Translation of KR-20210145046-A provided by PE2E (Year: 2021).*

* cited by examiner

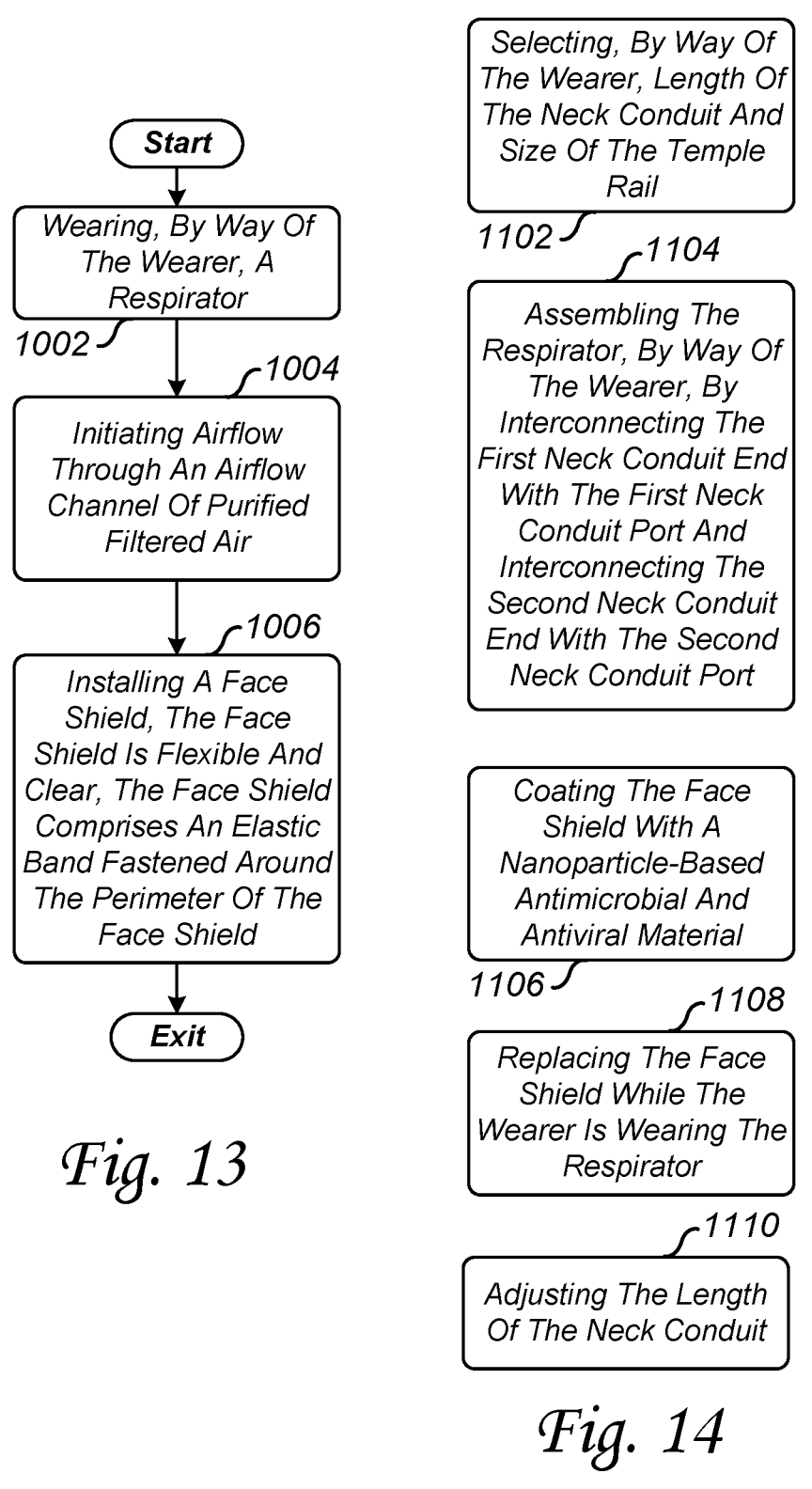

Start

Wearing, By Way Of The Wearer, A Respirator

1002

1004

Initiating Airflow Through An Airflow Channel Of Purified Filtered Air

1006

Installing A Face Shield, The Face Shield Is Flexible And Clear, The Face Shield Comprises An Elastic Band Fastened Around The Perimeter Of The Face Shield

Exit

*Fig. 13*

Selecting, By Way Of The Wearer, Length Of The Neck Conduit And Size Of The Temple Rail

1102

1104

Assembling The Respirator, By Way Of The Wearer, By Interconnecting The First Neck Conduit End With The First Neck Conduit Port And Interconnecting The Second Neck Conduit End With The Second Neck Conduit Port Coating The Face Shield With A Nanoparticle-Based Antimicrobial And Antiviral Material

1106

1108

Replacing The Face Shield While The Wearer Is Wearing The Respirator

1110

Adjusting The Length Of The Neck Conduit

*Fig. 14*

NECK-MOUNT POWERED RESPIRATOR

CROSS-REFERENCE TO RELATED APPLICATIONS

This application contains subject matter which is related to the subject matter of the following co-pending application. The below-listed application is hereby incorporated herein by reference in its entirety:

This is a U.S. non-provisional application that claims the benefit of a U.S. provisional application, Ser. No. 63/302,516, inventor Francis Palma Fabrigas, entitled "NECK-MOUNTABLE POWERED RESPIRATOR", filed Jan. 24, 2022.

TECHNICAL FIELD OF THE INVENTION

This invention relates to neck-mount powered respirators and methods of use. The respirators comprise an air handler, a temple rail, and a shoulder rail that fits around the back of the neck and over the shoulders of the wearer. The temple rail fits snugly around the back of the head and contacts the temples of the wearer. A neck conduit interconnects the shoulder rail and the temple rail forming a rigid structure with an airflow channel. A face shield includes an elastic band that covers the temple vents and the eyes, nose, and mouth of the wearer. Purified filtered air inflates the region between the face shield and the face of the wearer allowing the wearer to breathe the purified filtered air.

BACKGROUND OF THE INVENTION

Respiratory infections can be transmitted by an infected individual simply by sneezing, coughing, and even talking to the uninfected person who inadvertently inhales the infectious organism or infection-laden particles. Transmission may also happen when the virus or bacteria-laden particles enter an uninfected person's mouth, nose, or mucus membranes by cross-contamination via direct touch. Currently, some of the protective devices used to prevent infectious transmission are face shields, masks, and goggles.

A shortcoming of face masks, particularly the high-efficiency models such as N95 is that they restrict airflow which for some people makes it hard to breathe in and out. In addition, face masks are often pulled tight to the wearer's face which can cause pressure injuries to the face of the wearer.

A powered air-purifying respirator (PAPR) is another protective device used by medical personnel to protect themselves from airborne droplets that can transmit infections. PAPR devices include a filtering mechanism and a blower that directs filtered air to a semi-sealed chamber created between the wearer's face and the see-through facial barrier creating a positive pressure allowing the wearer to inhale clean, filtered air and at the same time protect the wearer's face from outside environment hazards however, currently, available PAPRs are expensive, time-consuming to set up, difficult to change face shields and filters, prevent the wearer from touching their face such as for scratching an itch, and cumbersome to wear and use.

In this regard, before protection starts, the wearer has to execute multiple steps which include putting on a helmet, adjusting a harness, putting on the belt that holds the power supply, adjusting the belt for proper fit, latching the power supply to the belt, hooking the power cord to the helmet and the power supply, attaching the facial shield or hood, checking again if the power cord is connected and fully secured and finally turning on the PAPR device. A shortcoming of these multiple steps is that it complicates the setup and takes much time and effort on the part of the wearer increasing the chance of errors that can put the wearer unsuspectingly in risky situations.

Another shortcoming of a multiple-step up process is that it reduces the wearer's efficiency on the job. In this regard, in fast-paced environments, such as medical and other environments, increasing the complexity and time of PAPR setup reduces the time the wearer is focusing on the job at hand. During a work day where the wearer is putting on and taking off PAPR devices multiple times the reduced job efficiency can be considerable and affect those the wearer is there to help such as patients and other people.

A shortcoming of prior powered air-purifying respirators is that they have integrated the fan motor, power supply, and filtering mechanisms in a helmet can feel bulky and become heavy on the head of the wearer even over time causing head and neck issues such as headache and neck strain.

A shortcoming of prior powered air respirators is that they don't allow the wearer to safely touch their face such as when they have an itch or in other situations.

The present invention addresses these and other shortcomings by providing a neck-mount powered respirator that provides full face protection and other advantages. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of a neck-mount powered respirator. The neck-mount powered respirator comprises at least one air handler. The air handler comprises a first neck conduit port, a filter port, and a blower motor. At least one removable filter interconnects with the filter port.

The neck-mount powered respirator further comprises a shoulder rail that is curvilinear and u-shaped. When worn by a wearer the shoulder rail fits around the back of the neck and over the shoulders of the wearer. The shoulder rail comprises a first shoulder rail end and a second shoulder rail end that when worn by the wearer are positioned proximate to the face of the wearer. A midpoint of the shoulder rail interconnects with the air handler in a manner that positions the air handler, when worn by the wearer, behind the neck of the wearer.

The neck-mount powered respirator further comprises a temple rail that is hollow, curvilinear, u-shaped, and sized, when worn by the wearer, to fit snugly around the back of the head and contact the temple of the wearer. The temple rail comprises a second neck conduit port, a temple vent at each end of the temple rail, and more than one face shield hook positioned on the outer surface of the temple rail proximate to the temple vent.

The neck-mount powered respirator further comprises a neck conduit that is hollow and curvilinear in shape. The neck conduit comprises a first neck conduit end and a second neck conduit end. The neck conduit interconnects, in a removable manner, the first neck conduit end with the first neck conduit port and the second neck conduit end with the second neck conduit port forming a rigid structure between the shoulder rail, the neck conduit, and the temple rail, and forming an airflow channel which ingresses an external air through the removable filter by way of the blower motor creating a purified filtered air, and transports the purified filtered air, inside the airflow channel and without contact with the external air, through the air handler, the neck conduit, and the temple rail, and egresses the purified filtered air from the temple vent.

The neck-mount powered respirator further comprises a face shield that is flexible and clear. The face shield comprises an elastic band fastened around the perimeter of the face shield. When worn by the wearer, the face shield stretches around and contacts the perimeter of the face covering the temple vents, and the wearer's eyes, nose, and mouth. The elastic band interconnects with each of the face shield hooks securing the face shield in position. The purified filtered air emitted from the temple vents inflates the region between the face shield and the face of the wearer allowing the wearer to breathe the purified filtered air.

Additional shortcomings of the prior art are overcome and additional advantages are provided through the provision of a neck-mount powered respirator. The neck-mount powered respirator comprises at least one air handler. The air handler comprises at least one filter port, and at least one blower motor. At least one removable filter interconnects with the filter port.

The neck-mount powered respirator further comprises a shoulder rail that is hollow, curvilinear, and u-shaped. When worn by a wearer, the shoulder rail fits around the back of the neck, and over the shoulders of the wearer, the shoulder rail comprises a first neck conduit port, a first shoulder rail end, and a second shoulder rail end. When worn by the wearer the first neck conduit port is positioned proximate to the back of the neck of the wearer, and the first shoulder rail and the second shoulder rail are positioned proximate to the face of the wearer. The air handler is integrated into either the first shoulder rail end or the second shoulder rail end.

The neck-mount powered respirator further comprises a temple rail that is hollow, curvilinear, u-shaped, and sized, when worn by the wearer, to fit snugly around the back of the head and contact the temple of the wearer. The temple rail comprises a second neck conduit port, a temple vent at each end of the temple rail, and more than one face shield hook positioned on the outer surface of the temple rail proximate to the temple vent.

The neck-mount powered respirator further comprises a neck conduit that is hollow and curvilinear in shape. The neck conduit comprises a first neck conduit end and a second neck conduit end. The neck conduit interconnects, in a removable manner, the first neck conduit end with the first neck conduit port and the second neck conduit end with the second neck conduit port forming a rigid structure between the shoulder rail, the neck conduit, and the temple rail, and forming an airflow channel which ingresses an external air through the removable filter by way of the blower motor creating a purified filtered air, and transports the purified filtered air, inside the airflow channel and without contact with the external air, through the air handler, the shoulder rail, the neck conduit, and the temple rail, and egresses the purified filtered air from the temple vent.

The neck-mount powered respirator further comprises a face shield that is flexible and clear. The face shield comprises an elastic band fastened around the perimeter of the face shield. When worn by the wearer, the face shield stretches around and contacts the perimeter of the face covering the temple vents, and the wearer's eyes, nose, and mouth. The elastic band interconnects with each of the face shield hooks securing the face shield in position. The purified filtered air emitted from the temple vent inflates a region between the face shield and the face of the wearer allowing the wearer to breathe the purified filtered air.

Additional shortcomings of the prior art are overcome and additional advantages are provided through the provision of a method of using a neck-mount powered respirator. The method comprises the step of wearing, by way of a wearer, a respirator. The respirator comprises at least one air handler. The air handler comprises at least one filter port and at least one blower motor. At least one removable filter interconnects with the filter port. A shoulder rail is curvilinear and u-shaped. When worn by the wearer, the shoulder rail fits around the back of the neck and over the shoulders of the wearer. The shoulder rail comprises a first shoulder rail end and a second shoulder rail end that when worn by the wearer are positioned proximate to the face of the wearer, in one of the following ways, either a midpoint of the shoulder rail interconnects with the air handler in a manner that positions the air handler, when worn by the wearer, behind the neck of the wearer, and the air handler comprises a first neck conduit port, or the shoulder rail is hollow and comprises the first neck conduit port and the air handler is integrated into either the first shoulder rail end or the second shoulder rail end.

The method then continues with the step of initiating airflow through an airflow channel of purified filtered air. A temple rail is hollow, curvilinear, u-shaped, and sized, when worn by the wearer, to fit snugly around the back of the head and contact the temple of the wearer. The temple rail comprises a second neck conduit port, a temple vent at each end of the temple rail, and more than one face shield hook positioned on the outer surface of the temple rail proximate to the temple vent. A neck conduit is hollow and curvilinear in shape. The neck conduit comprises a first neck conduit end and a second neck conduit end. The neck conduit interconnects, in a removable manner, the first neck conduit end with the first neck conduit port and the second neck conduit end with the second neck conduit port forming a rigid structure between the shoulder rail, the neck conduit, and the temple rail, and forming the airflow channel in one of the following ways by ingressing an external air through the removable filter by way of the blower motor creating a purified filtered air, and transports the purified filtered air, inside the airflow channel and without contact with the external air, through the air handler, the neck conduit, and the temple rail, and egresses the purified filtered air through the temple vent, or by ingressing the external air through the removable filter by way of the blower motor creating the purified filtered air, and transports the purified filtered air, inside the airflow channel and without contact with the external air, through the air handler, the shoulder rail, the neck conduit, and the temple rail, and egresses the purified filtered air from the temple vent.

The method then continues with the step of installing a face shield. The face shield is flexible and clear. The face shield comprises an elastic band fastened around the perimeter of the face shield. When worn by the wearer, the face shield stretches around and contacts the perimeter of the face of the wearer covering the temple vents, and the eyes, nose, and mouth of the wearer, the elastic band interconnects with each of the face shield hook securing the face shield in position. The purified filtered air emitted from the temple vents inflates the region between the face shield and the face of the wearer allowing the wearer to breathe the purified filtered air.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 13 illustrates one example of a method of using a neck-mount powered respirator; and FIG. 14 illustrates exemplary embodiments that can be interchangeably used with the methods of the present invention.

The detailed description explains the preferred embodiments of the invention, together with advantages and features, by way of example with reference to the drawings.

DETAILED DESCRIPTION OF THE INVENTION

An advantage, in the present invention, is to provide a powered air respirator that protects the wearer from inhaling pathogen-laden particulates from ambient air and to provide facial protection that protects the wearer's face from particulates from coughing and sneezing of other people. The present invention also provides a powered respirator that has an integrated power supply and air filtering mechanism without the need for trailing cable and/or hose. The present invention also involves fewer setup steps and less time for a wearer to put on to achieve optimum respiratory protection versus prior respirators. Furthermore, the present invention provides methods of use that lessens the steps taken by the clinician wearer to wear the neck-mount powered respirator so that they can more quickly attend to the needs of a patient.

Figure 1:
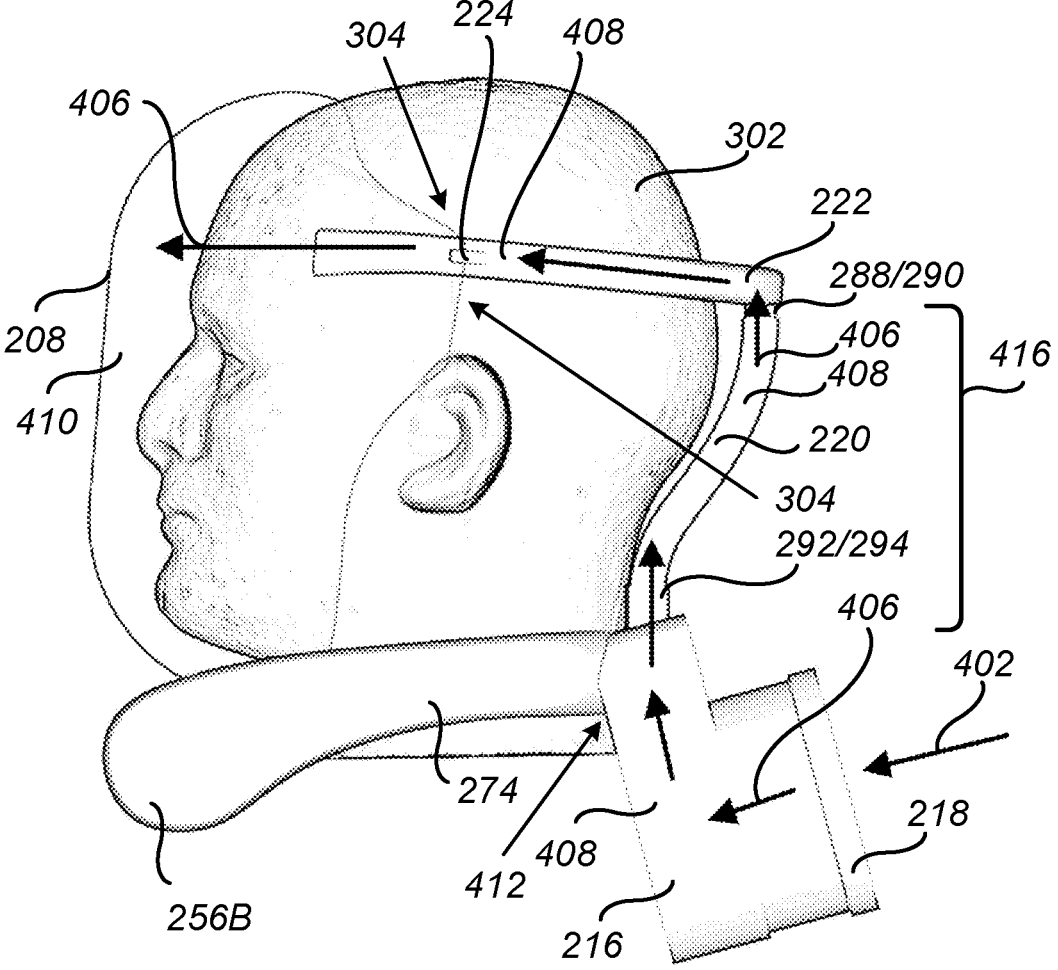
FIG. 1 illustrates one example of a left-side view of a neck-mount powered respirator being worn by a wearer.

Turning now to the drawings in greater detail, it will be seen that in FIG. 1 there is illustrated one example of a left-side view of a neck-mount powered respirator being worn by a wearer. In an exemplary embodiment, the neck-mount powered respirator 200 also referred to as respirator 200 is illustrated showing how external air 402 enters the respirator 200 through the removable air filter 218 assembly creating a purified filter air 406 that is absent airborne particulates, bacteria, viruses, other pathogens or microorganisms, and/or other airborne contaminates. Propelled by the blower motor 230 and traveling in an airflow channel 408 formed inside the respirator components and not contacting the external air 402, the purified filtered air 406 moves through the air handler 216, the neck conduit 220, and the temple rail 222 to egress or otherwise be discharged in the region 410 between the face shield 208 and the face of the wearer providing the wearer 302 a continuous supply of purified filter air 406 to breathe. The mixture of purified filtered air 406 and wearer 302 exhaled air exits through a space created between the wearer's 302 temples 304, the temple rails 222, and the elastic 210 sealing edge of the face shield 208 over the temple rail 222 proximate to the temple vents 246 and around the perimeter of the face of the wearer 302.

In the present invention, in a plurality of exemplary embodiments, there are at least two different ways to configure air channel 408. In both configurations, air channel 408 is formed within the hollow portion of the interconnected components. In this regard, in one embodiment, the air handler 216 is positioned on the neck of the wearer 302 as better illustrated in at least FIG. 1, the air channel 408 is formed by the air handler 216, the neck conduit 220, and the temple rail 222, each is hollow and interconnected together forming the air channel 408. And in a second embodiment, the air handler 216 is integrated into the shoulder rail 274 as better illustrated in at least FIG. 12, the air channel 408 is formed by the air handler 216, shoulder rail 274, the neck conduit 220, and the temple rail 222, each is hollow and interconnected together forming the air channel 408.

In an exemplary embodiment, a neck-mount powered respirator 200 can comprise at least one air handler 216. The air handler 216 can comprise a first neck conduit port 292, a filter port 244 better illustrated in at least FIG. 7, and a blower motor 230. At least one removable filter 218 interconnects with filter port 244. A shoulder rail 274 can be curvilinear and u-shaped. When worn by a wearer 302 the shoulder rail 274 fits around the back of the neck and over the shoulders of the wearer 302.

In the present invention, an advantage is that the respirator 200 mounts around the neck and rests on the shoulders of the wearer 302. This allows the weight of the respirator 200, which is minimal in the present invention, to be carried on the shoulders of the wearer 200 rather than in prior respirators which are much heavier and carried on the head of the wearer which can cause fatigue as well as cause shoulder and neck problems when worn for extended periods of time.

Figure 4:
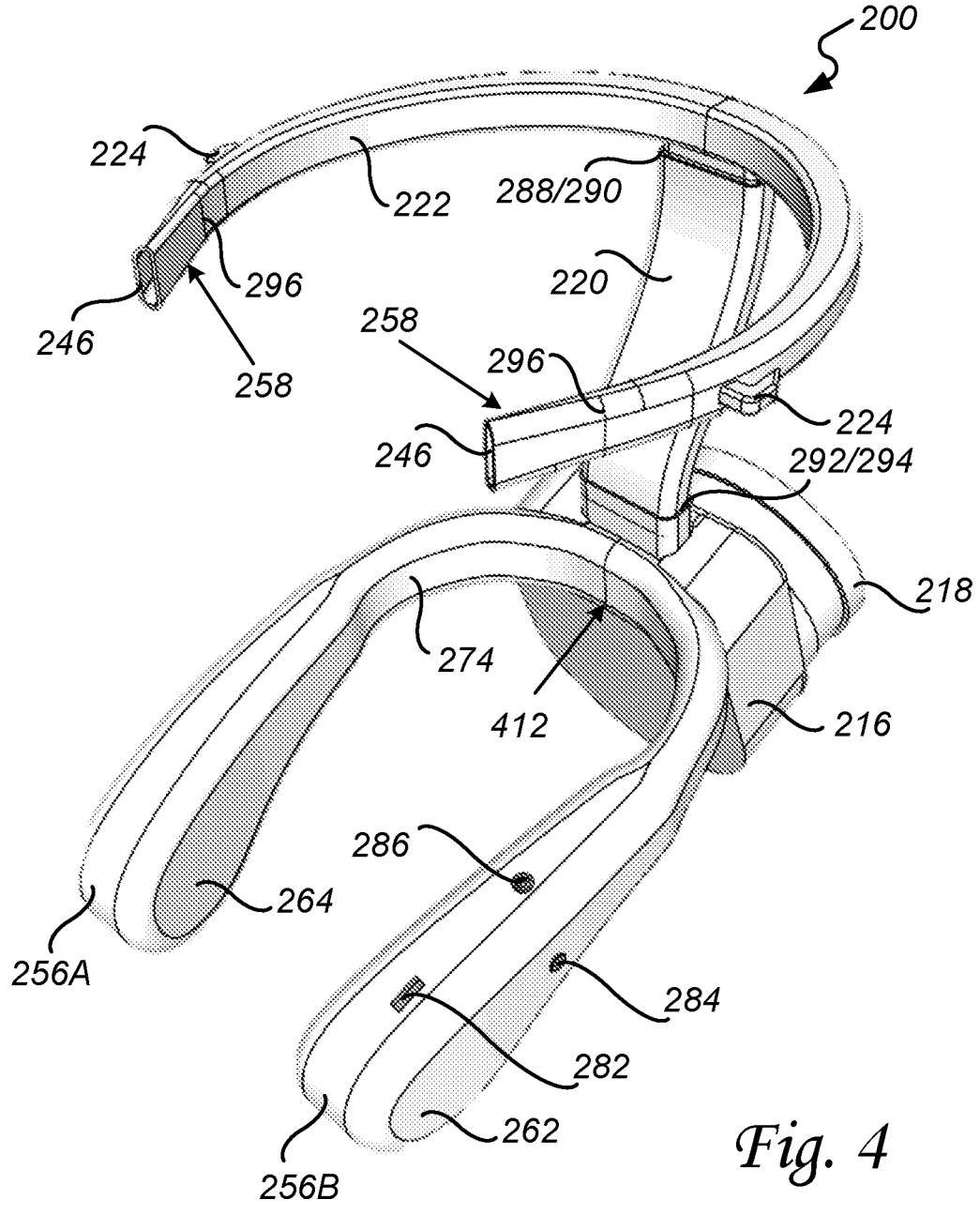
FIG. 4 illustrates one example of a front-left perspective view of a neck-mount powered respirator absent the face shield.
Figure 5:
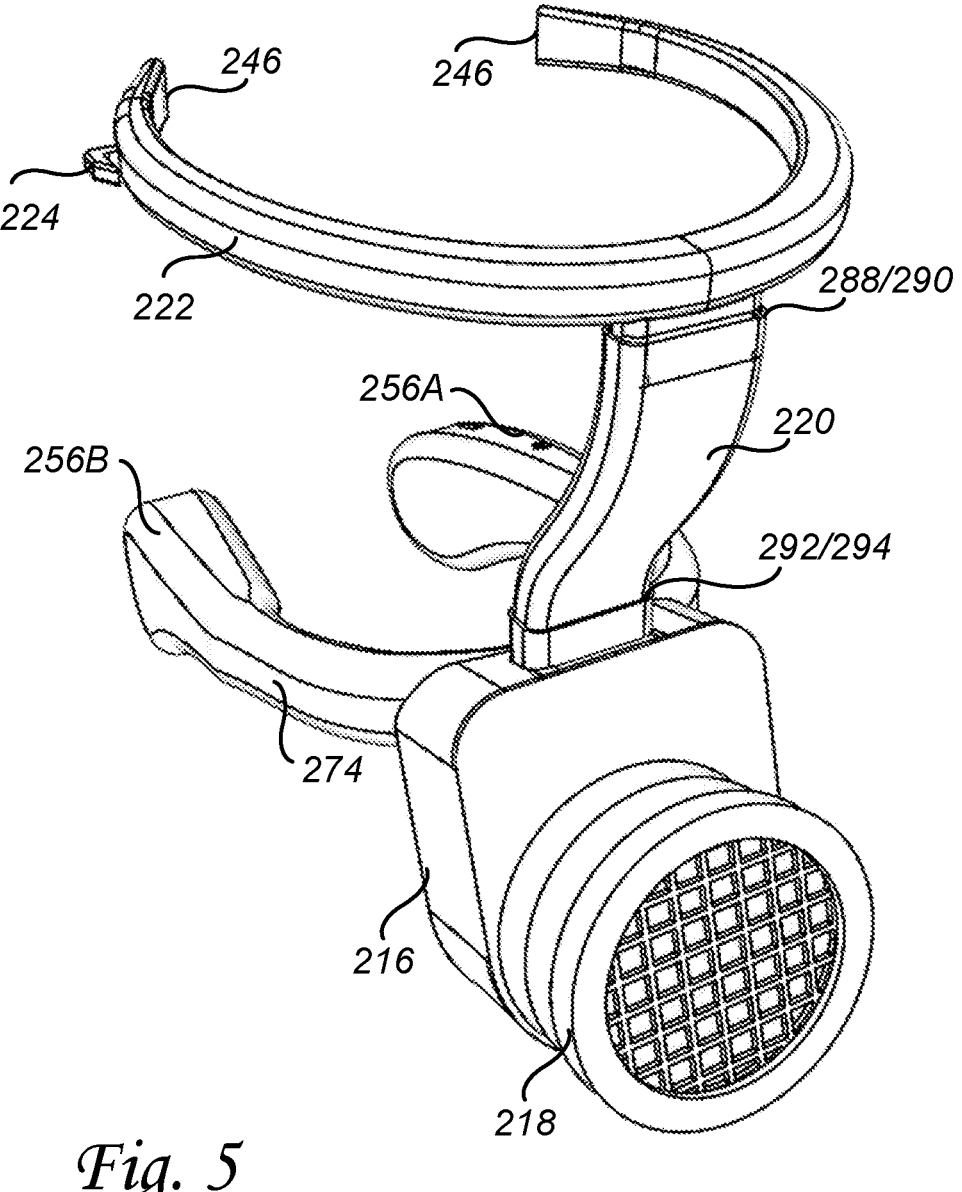
FIG. 5 illustrates one example of a back-left perspective view of a neck-mount powered respirator absent the face shield.

Referring to FIG. 4, there is illustrated one example of a front-left perspective view of a neck-mount powered respirator 200 absent the face shield 208. And in FIG. 5, there is illustrated a back-left perspective view of a neck-mount powered respirator 200 absent the face shield 208. In an exemplary embodiment, the shoulder rail 274 can comprise a first shoulder rail end 256A and a second shoulder rail end 256B that when worn by the wearer 302 the first shoulder end 256A and the second shoulder end 256B are positioned proximate to the face of the wearer 302. A midpoint 412 of the shoulder rail 274 interconnects with the air handler 216 in a manner that positions the air handler 216, when worn by the wearer 302, behind the neck of the wearer 302.

In an exemplary embodiment, a temple rail 222 is hollow, curvilinear, u-shaped, and sized, when worn by the wearer 302, to fit snugly around the back of the head and contact the temple of the wearer 302. The temple rail 222 comprises a second neck conduit port 288, a temple vent 246 at each end of the temple rail 222, and more than one face shield hook 224 positioned on the outer surface of the temple rail 222 proximate to the temple vents 246.

In an exemplary embodiment, the temple rail 222 can be formed with at least one flat surface portion 258. The flat surface portion 258 can be positioned to be in contact with the temple 304 of the wearer 302 to provide motion-free fit and stabilization of the respirator 200 when being worn by the wearer 302. In operation, the flat surface portion 258 provides a sufficiently large contacting surface that creates greater friction between the temple rail 222 and the temple 304 of the wearer 302. In addition, the force created by the temple rail 222 slightly squeezing the temple 304 of the wearer 302 is distributed across a larger surface making the respirator 200 more comfortable to wear by the wearer 302, particularly for long periods of time or in applications where the wearer 302 takes the respirator 200 'ON' and 'OFF' frequently over a long period of time, such as is common in the medical profession and other professions.

In an exemplary embodiment, a neck conduit 220 is hollow and curvilinear in shape. The neck conduit 220 comprises a first neck conduit end 294 and a second neck conduit end 290. The neck conduit 220 interconnects, in a removable manner, the first neck conduit end 294 with the first neck conduit port 292 and the second neck conduit end 290 with the second neck conduit port 288 forming a rigid structure between the shoulder rail 274, the neck conduit 220, and the temple rail 222, and forming an airflow channel 408 which ingresses an external air 402 through the removable filter 218 by way of the blower motor 230 creating a purified filtered air 406, and transports the purified filtered air 406, inside the airflow channel 408 and without contact with the external air 406, through the air handler 216, the neck conduit 220, and the temple rail 222, and egresses the purified filtered air 406 from the temple vents 246.

In an exemplary embodiment, at least one airflow tip 296 can be interconnected with the temple vent 246. The airflow tip redirects or otherwise positions the air flow stream of the purified filtered air 406 with respect to the eyes of the wearer 302 within the region 410 between the face shield 208 and the face of the wearer 302. In this regard, for wearers 302 that wear glasses, experience dry eyes, or for other reasons, the airflow tips 296 can redirect the stream of the purified filtered air 406 in a manner that prevents the air stream from hitting the inside of the glasses lenses or otherwise directing the continuous airflow of the purified filtered air 406 too close to the eyes of the wearer 302 in an irritating manner.

Figures 2, 3:
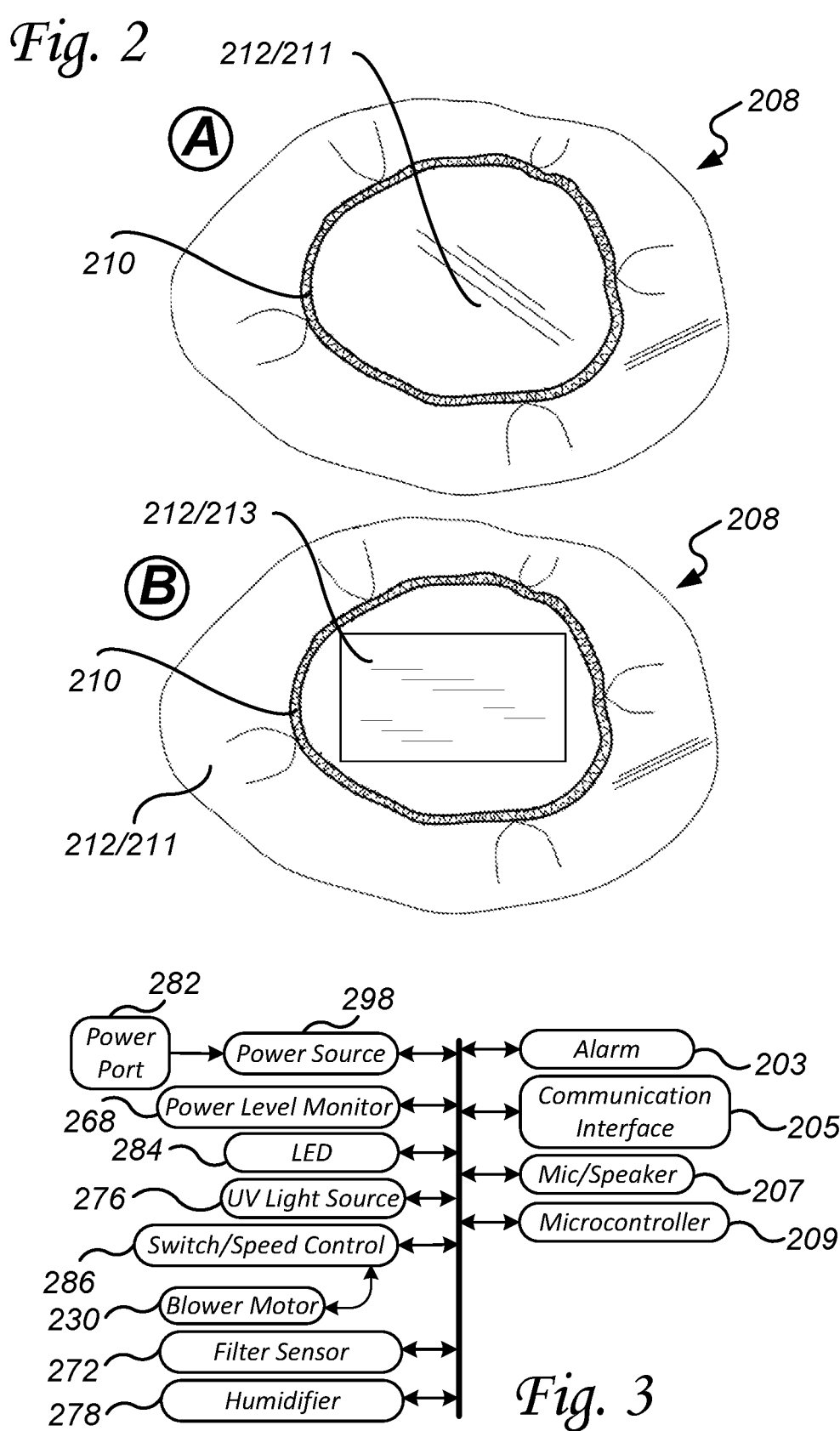
FIG. 2 illustrates one example of a face shield.
FIG. 3 illustrates one example of a respirator control system block diagram.

Referring to FIG. 2 and with reference to 'A', there is illustrated one example of a face shield 208. In an exemplary embodiment, a face shield 208 is fabricated from a flexible and clear material 211. The face shield 208 comprises an elastic band 210 that is fastened around the perimeter of the face shield 208. When worn by the wearer 302, the face shield elastic band 210 stretches around and contacts the perimeter of the face of the wearer 302 covering a portion of the temple rails 222 including the temple vents 246, and the eyes, nose, and mouth of the wearer 302. The elastic band 210 interconnects with each of the face shield hooks 224 securing the face shield 208 in position and preventing the face shield 208 from slipping off of the temple rail 222 exposing the temple vents 246 or otherwise allowing external air 402 to ingress the region 410 between the face shield 208 and the face of the wearer 302. In operation, the purified filtered air 406 emitted from the temple vents 246 inflates the region 410 between the face shield 208 and the face of the wearer 302 allowing the wearer 302 to breathe the purified filtered air 406.

In other exemplary embodiments and with reference to 'B', the face shield 208 can be comprised of bendably rigid 213 and flexible materials 211, wherein a thin ultra-clear bendably rigid material 213 can be centrally located where the wearer 302 looks through when wearing the face shield 208 and flexible material 211, with the elastic band 210, is used around the perimeter of the bendably rigid material 210 to aid in fitting the face of wearer 302 and interconnecting the face shield 208 elastic bands 210 with the face shield hooks 224.

In other exemplary embodiments and with reference to 'B', the face shield 208 can be comprised of bendably rigid 213 and flexible 211 materials, wherein in embodiments where the bendably rigid material 213 is proximate the face shield hooks 224, an attachment lever, clip, perforation in the bendably rigid 213 material, or other suitable method can be used to coupled and secured the face shield 208 to the temple rail 222.

In an exemplary embodiment, the face shield hooks 224 are configured to point towards the back of the head of the wearer 302 so that the as positive air pressure builds between the face shield 208 and the face of the wearer 302 in region 410 urging the face shield forward away from the face of the wearer 302, the hooks are orientated to grasp the elastic band 210 retarding the movement of the face shield 208, holding the face shield 208 stationary along the contacting perimeter edge of the face of the wearer 302.

In an exemplary embodiment, the face shield can be coated 212 with a nanoparticle-based antimicrobial and antiviral material. In this regard, such coating 212 can kill bacteria, viruses, and other pathogens and/or microorganisms on contact further reducing the risk of the wearer 302 breathing airborne particulates, bacteria, viruses, other pathogens or microorganisms, and/or other airborne contaminants.

Referring to FIG. 3, there is illustrated one example of a respirator control system block diagram. In a plurality of exemplary embodiments, features of the respirator control system can be configured as may be required and/or desired in a particular embodiment including excluding a feature that is not needed for a particular embodiment. As an example, and not a limitation should the respirator control system, in a particular embodiment, not require microphone/speaker 207 then the microphone/speaker 207 can be excluded from the configuration for that embodiment.

In an exemplary embodiment, a respirator control system can comprise interconnected and/or operationally related a microcontroller 209, a power source 298, a power level monitor 268, the blower motor 230, a light emitting diode (LED) 284, an alarm 203, a communicator interface 205, a microphone/speaker 207, an ultraviolet (UV) light source 276, a filter sensor 272, a humidifier 278, and a switch or a speed controller 286. In operation, wearer 302 can use the switch or a speed control 286 to turn 'ON' the respirator 200 and/or control the speed of the blower 130 which in turn controls the purified filtered air 406 airflow rate. In the 'ON' mode of operation, the blower motor 230 draws external air 402 through the removable filter 218 to create purified filtered air 406 that is absent of airborne particulates, bacteria, viruses, other pathogens or microorganisms, and/or other airborne contaminates. In operation, the switch or the speed control 286 can be accessible to the wearer 302 proximate to the first shoulder rail end 256A or the second shoulder rail end 256B or positioned in other locations as may be required and/or desired in a particular embodiment.

In an exemplary embodiment, a power source 298 can be a battery, a rechargeable battery, including a solar panel to effectuate charging the rechargeable battery, or other suitable power sources as may be required and/or desired in a particular embodiment.

In an exemplary embodiment, a power level monitor 268 can monitor and display the amount of remaining charge in the battery or other power source 298. Such display can be LED light or other suitable indicator as may be required and/or desired in a particular embodiment.

The microcontroller 209 can be an INTEL, ZILOG, MICROCHIP, AMD, ARM, and/or other types or kinds of microcontrollers.

Additionally, a power port 282 can allow an external power source such as an AC or DC transformer to be coupled to the respirator to provide power permanently during use or temporarily just to recharge the rechargeable batteries.

In an exemplary embodiment, the LED 284 can be configured as a respirator 200 'ON'/'OFF' indicator and/or configured as a time to change the removable filter 218 reminder indicator light.

In an exemplary embodiment, a UV light source 276 can be positioned within the airflow channel 408 to provide a way to inactivate microorganisms and pathogens as air flows through airflow channel 408.

In an exemplary embodiment, a filter sensor 272 can be configured to monitor the removable filter 218 to determine when the removable filter 218 needs to be changed. Such monitoring can be based on measuring operating or run time of the blower motor 230, by sensor level inspection of the filter material 238 attributes such as airflow rate, cleanliness, or other attribute, or configured to determine when the removable filter 218 needs to be changed in other ways as may be required and/or desired in a particular embodiment.

In an exemplary embodiment, a humidifier 278 can be integrated into the respirator 200 and configured to control the humidity of the purified filter air 406. In operation, purified filtered air 406 that is too dry or too moist can be irritating to a wearer 302. The humidifier 278, in the present invention, can be configured to control the humidity to create a comfortable purified filtered air 406 breathing experience for the wearer 302.

The alarm 203 can be noise lights, voice recording, relays, siren, horn, piezo buzzer, speaker, voice annunciations, and/or other types and kinds of audible alarms.

The communication interfaces 205 can be LAN, WAN, USB, Ethernet, RS232, RS485, serial, WiFi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

The microphone and speaker 207 aren't particularly limited and can be any suitable type of microphone and speaker as may be required and/or desired in a particular embodiment.

Figure 6:
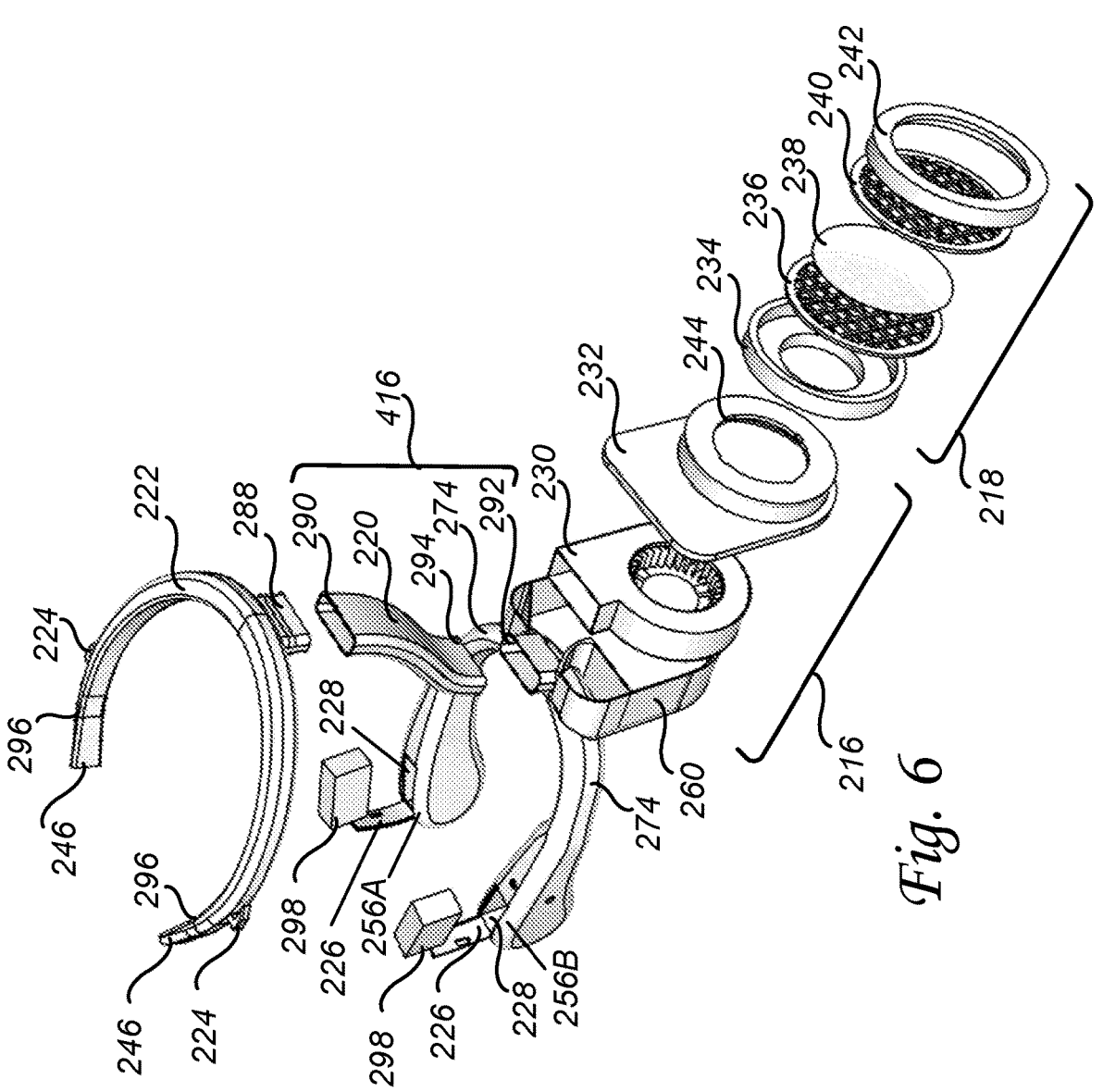
FIG. 6 illustrates one example of a back-left perspective exploded view of a neck-mount powered respirator absent the face shield.

Referring to FIG. 6, there is illustrated one example of a back-left perspective exploded view of a neck-mount powered respirator 200 absent the face shield 208. In an exemplary embodiment, the removable filter 218 can comprise at least one filter material 238, at least one filter screen 236/240, and a filter enclosure 234/242. The filter material 238, and the filter screens 236/240 are enclosed within the filter enclosure 234/242.

Figure 7:
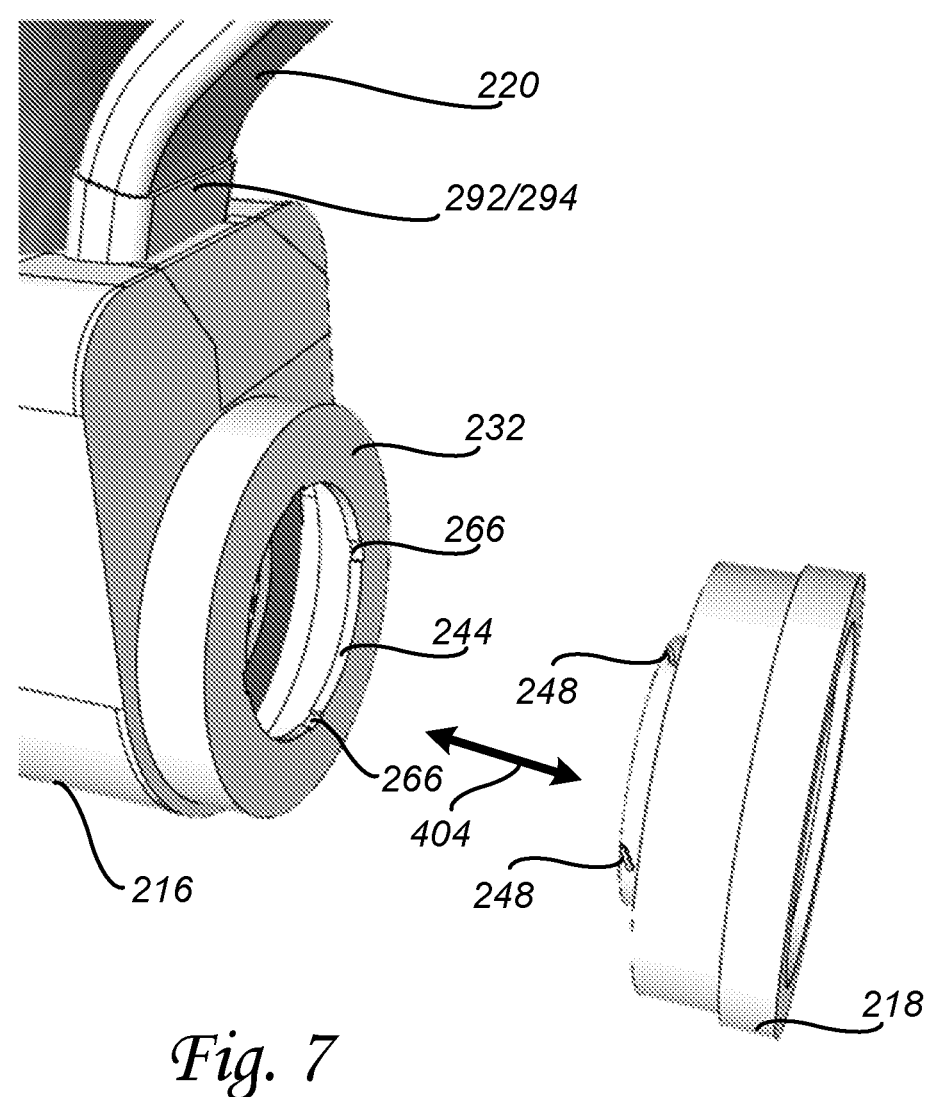
FIG. 7 illustrates one example of the interconnection between an air handler and a removable filter.
Figure 8:
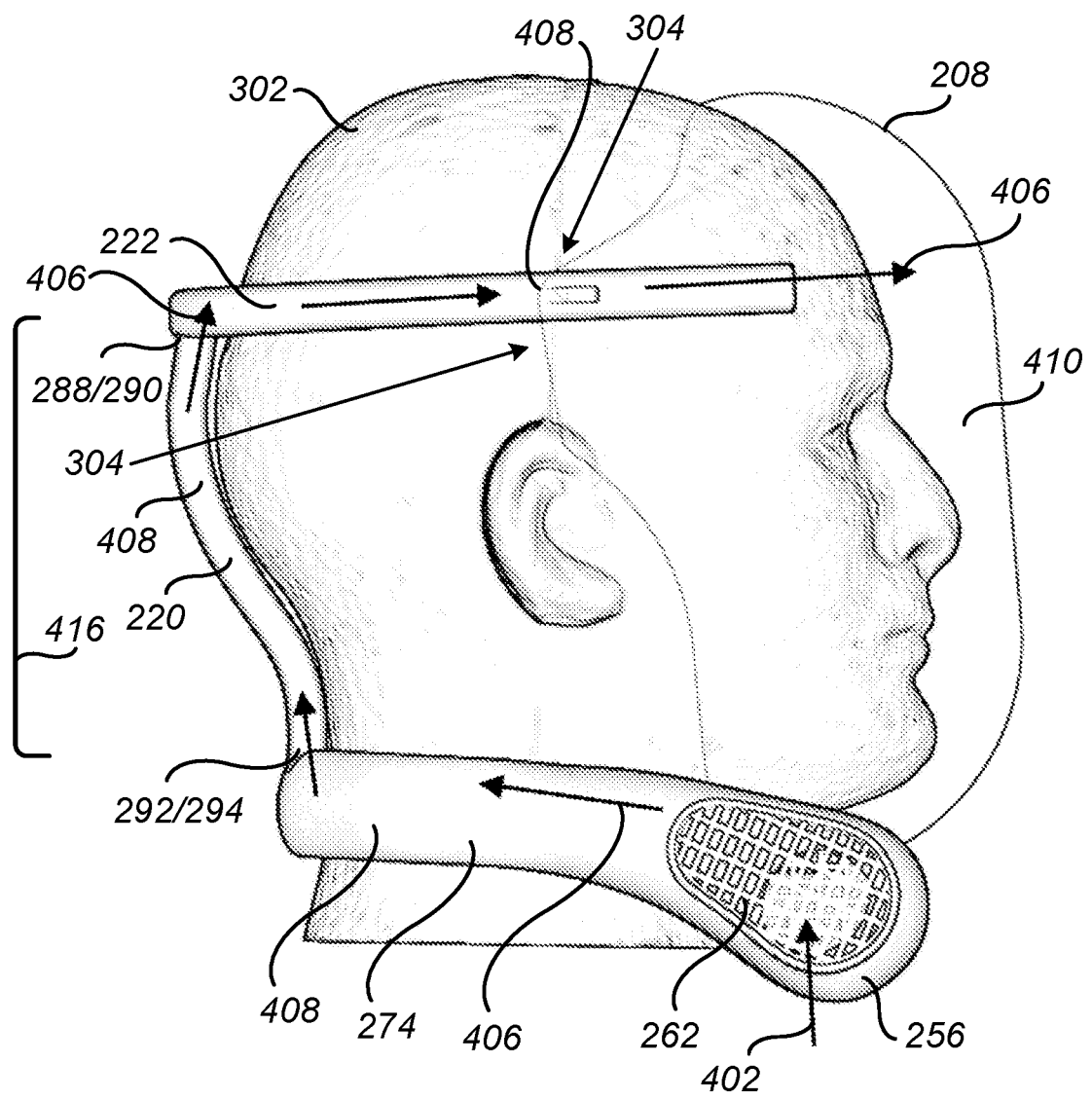
FIG. 8 illustrates one example of a right-side view of a neck-mount powered respirator on a wearer.

With reference to at least FIG. 7, in an exemplary embodiment, the removable filter 218 formed by the filter enclosure 234/242 can be configured to insert 404 and rotate to removably fasten the removable filter 218 within the filter port 244. In this regard, FIG. 7 illustrates one example of the interconnection between an air handler 216 and a removable filter 218. In an exemplary embodiment, locking teeth 248 can insert through locking teeth notches 266, and then by rotating, the locking teeth 248 secure the removable filter 218 within the filter port 244.

In an exemplary embodiment, the air handler 216 can comprise an air handler base 260, a blower motor 230, and an air handler cover 232. The air handler base 260 and the air handler cover 232 forms an enclosure that the blower motor 230 fits within. The filter port 244 can be integrally formed in the air handler cover 232.

In an exemplary embodiment, filter material 238 can be a single layer of filter material or a composition of several layers of filter material. The filter materials can be of varying pore size, adapted to filter particulates and/or gases, and can include other types of venting as may be required and/or desired in a particular embodiment. The filter material 238 is capable of performing sufficient filtering of external air 402 to produce an N95-compliant or better purified filtered air 406 supply for the wearer 302 to breathe.

In an exemplary embodiment, the length 416 of the neck conduit 220 is adjustable to fit the neck length as well as the distance between the shoulders and the temples 304 of the wearer 302. In this regard, the neck conduit 220 can be adjusted in length to best fit the wearer 302. In some embodiments, a way to adjust the length of the neck conduit 220 can be to offer different sizes of the neck conduit 220 such as small, medium, and large. In this regard, the wearer 302 can select the length that best fits their shoulder, neck, and head anatomy. In other embodiments, a way to adjust the length of the neck conduit 220 can be to form the neck conduit 220 in more than one movable segment that allows the segments to telescope 'IN' and 'OUT' to shorten or lengthen the neck conduit 220 when the wearer 302 pulls on the ends of the neck conduit 220. In other embodiments, a way to adjust the length of the neck conduit 220 can be by allowing the first neck conduit end 294 and the first neck conduit port 292 and/or the second neck conduit end 290 and the second neck conduit port 288 to be ribbed and grooved as to allow the interconnections to click into more than one position to shorten or lengthen the distance between the shoulder rail 274 and the temple rail 222.

In an exemplary embodiment, the first shoulder rail end 256A or the second shoulder rail end 256B or both comprise a compartment 228 having a lid 226 for storing the power source 298 and other electronic components.

In an exemplary embodiment, the respirator components including the air handler 216, removable filter 218, face shield 208, shoulder rail 274, neck conduit 220, and temple rail 222 can be fabricated from plastic, metal, polymers, rubber, glass, a fabric, combination thereof, or other suitable materials.

Figure 9:
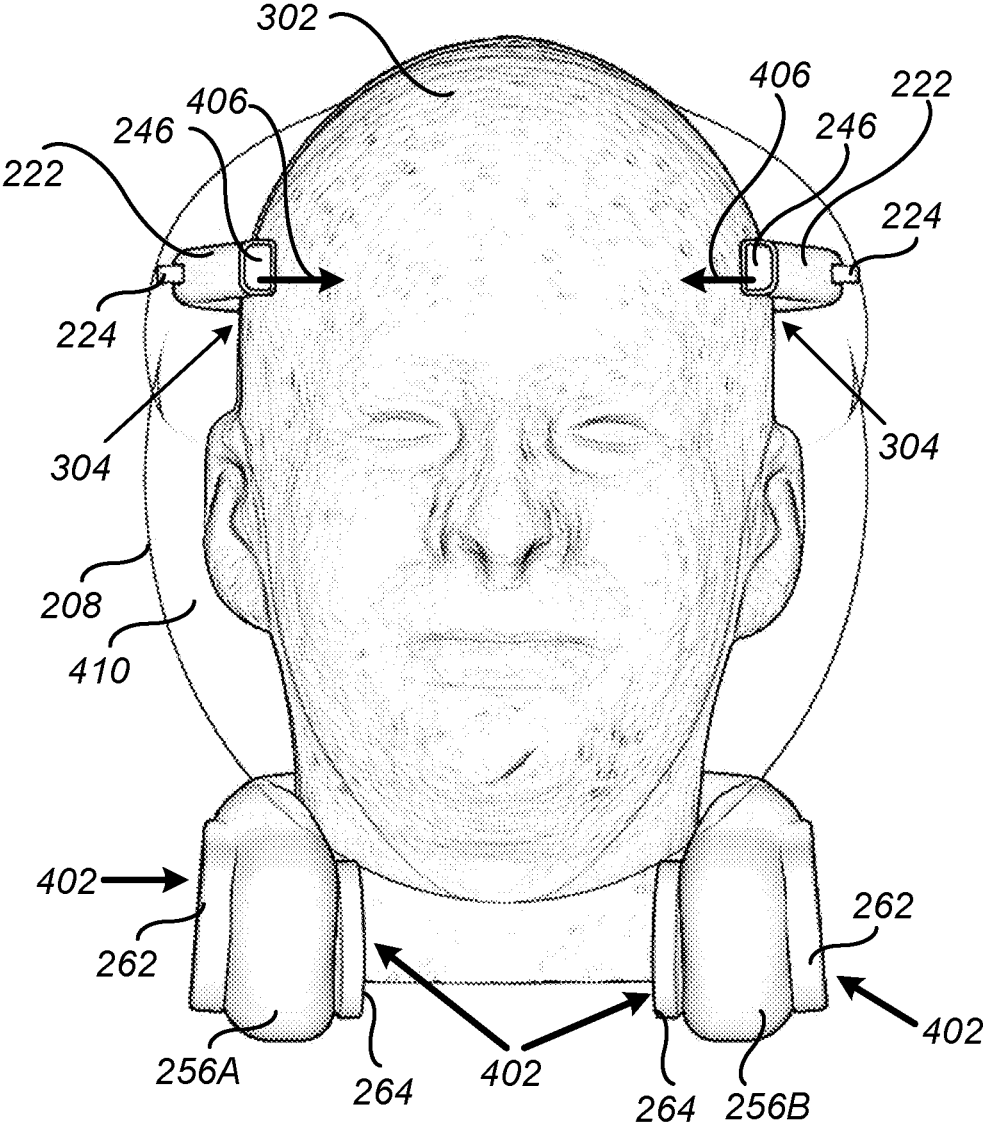
FIG. 9 illustrates one example of a front view of a neck-mount powered respirator.
Figure 10:
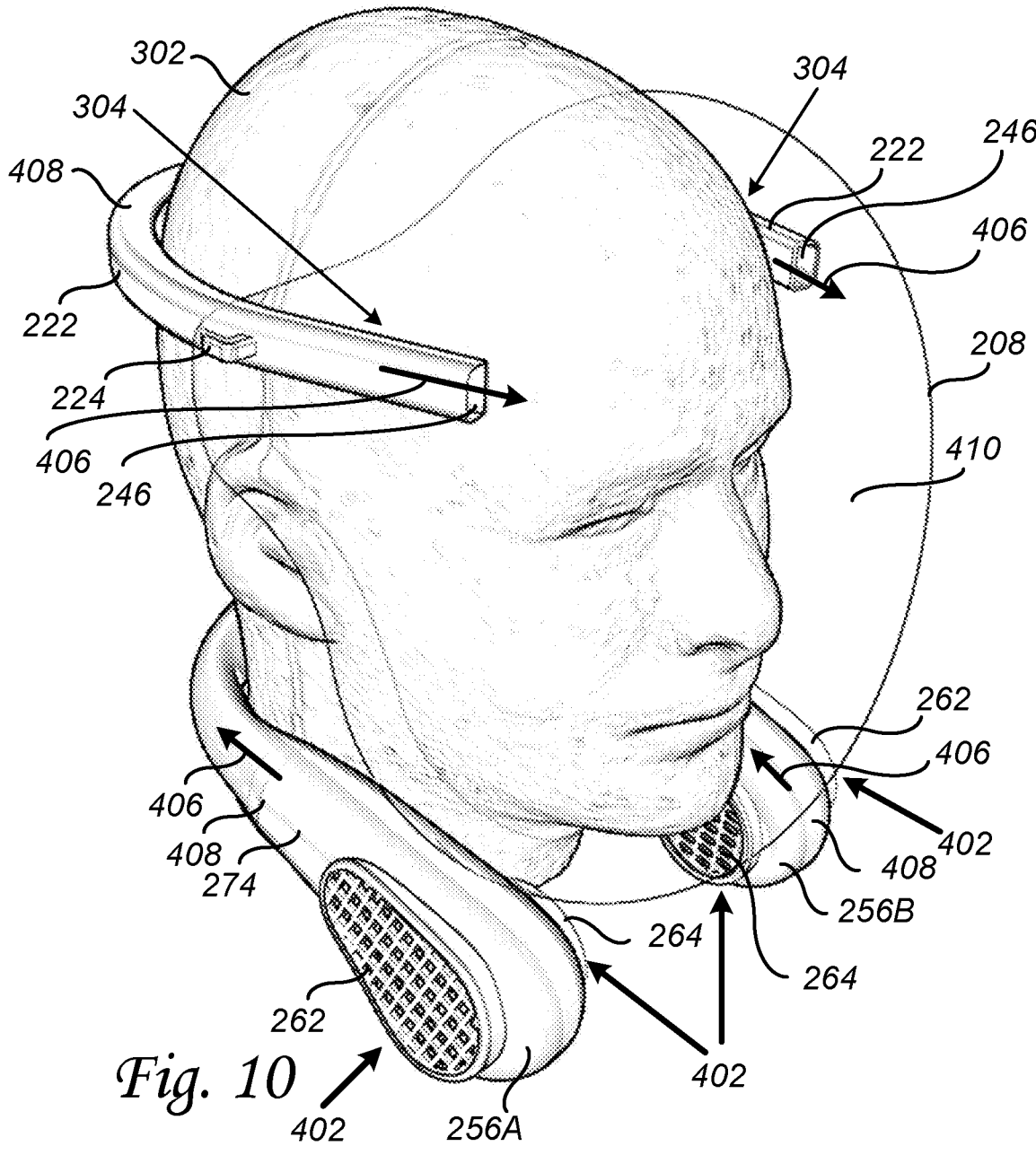
FIG. 10 illustrates one example of a front-right perspective view of a neck-mount powered respirator.
Figure 11:
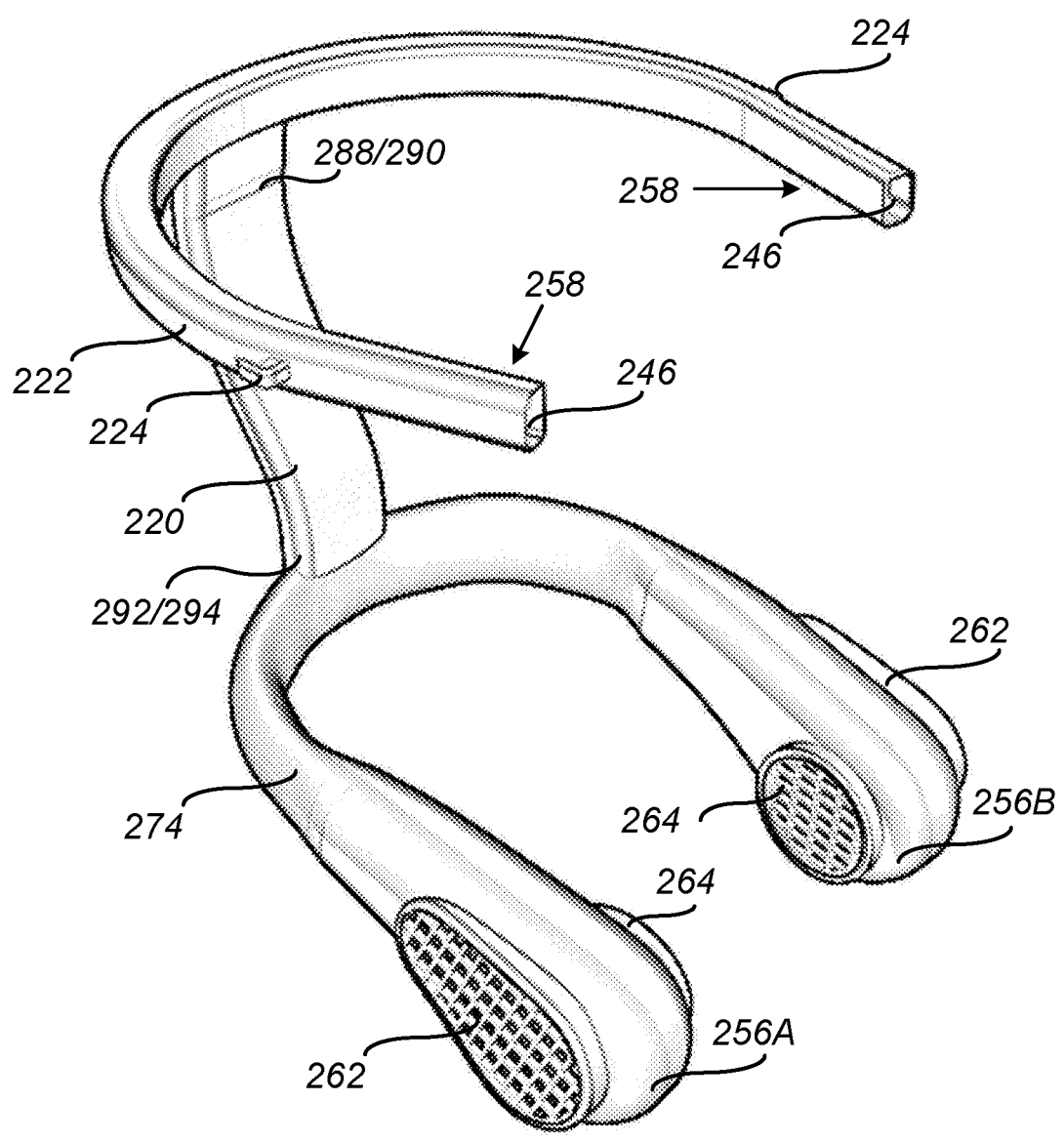
FIG. 11 illustrates one example of a front-right perspective view of a neck-mount powered respirator absent the face shield.
Figure 12:
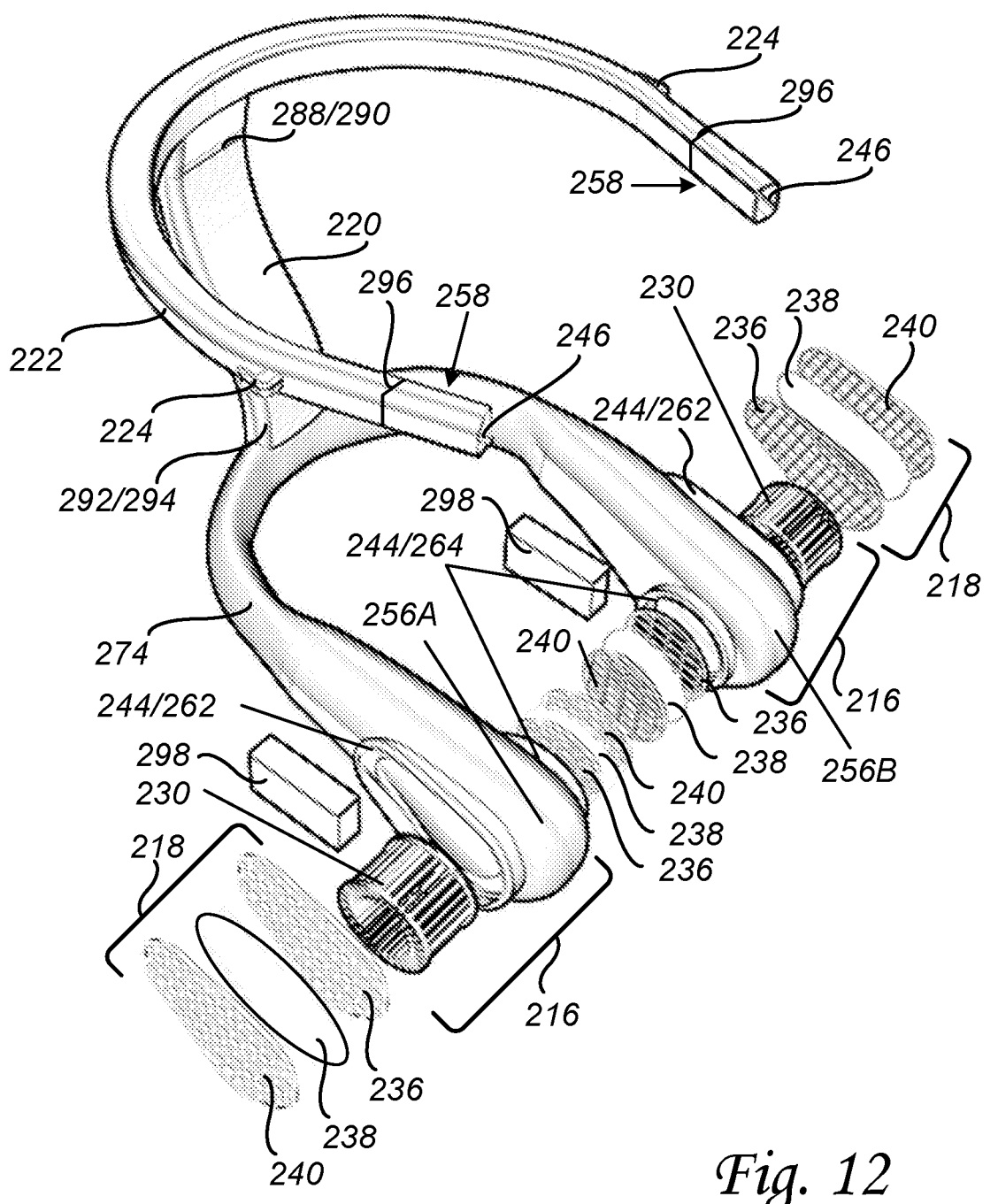
FIG. 12 illustrates one example of a front-right perspective exploded view of a neck-mount powered respirator absent the face shield.

Referring to FIGS. 8-12, FIG. 8 is illustrated one example of a right-side view of a neck-mount powered respirator 200. FIG. 9 illustrates one example of a front view of a neck-mount powered respirator 200. FIG. 10 illustrates one example of a front-right perspective view of a neck-mount powered respirator 200. FIG. 11 illustrates one example of a front-right perspective view of a neck-mount powered respirator 200 absent the face shield 208. And, FIG. 12 illustrates one example of a front-right perspective exploded view of a neck-mount powered respirator 200 absent the face shield 208. In an exemplary embodiment, a neck-mount powered respirator 200 can comprise at least one air handler 216. The air handler 216 can comprise at least one filter port 244, and at least one blower motor 230. At least one removable filter 218 interconnects with filter port 244.

In an exemplary embodiment, a shoulder rail 274 is hollow, curvilinear, and u-shaped. When worn by a wearer 302 the shoulder rail 274 fits around the back of the neck and over the shoulders of the wearer 302. The shoulder rail 274 comprises a first neck conduit port 292, a first shoulder rail end 256A, and a second shoulder rail end 256B. When the shoulder rail 274 is worn by the wearer 302 the first neck conduit port 292 is positioned proximate to the back of the neck of the wearer 302, and the first shoulder rail 256A and the second shoulder rail 256B are positioned proximate to the face of the wearer 302. In an exemplary embodiment, the air handler 216 is integrated into either the first shoulder rail end 256A, the second shoulder rail end 256B, or both in the case where more than one air handler 216 is implemented in an embodiment.

In an exemplary embodiment, a temple rail 222 is hollow, curvilinear, u-shaped, and sized, when worn by the wearer 302, to fit snugly around the back of the head and contact the temple 304 of the wearer 302. The temple rail 222 comprises a second neck conduit port 288, a temple vent 246 at each end of the temple rail 222, and more than one face shield hook 224 positioned on the outer surface of the temple rail 222 proximate to the temple vents 246.

In an exemplary embodiment, a neck conduit 220 is hollow and curvilinear in shape. The neck conduit 220 comprises a first neck conduit end 294 and a second neck conduit end 290. The neck conduit 220 interconnects, in a removable manner, the first neck conduit end 294 with the first neck conduit port 292 and the second neck conduit end 290 with the second neck conduit port 288 forming a rigid structure between the shoulder rail 274, the neck conduit 220, and the temple rail 222, and forming an airflow channel 408 which ingresses an external air 402 through the removable filter 218 by way of the blower motor 230 creating a purified filtered air 406, and transports the purified filtered air 406, inside the airflow channel 408 and without contact with the external air 402, through the air handler 216, the shoulder rail 274, the neck conduit 220, and the temple rail 222, and egresses the purified filtered air 406 from the temple vents 246.

In an exemplary embodiment, a face shield 208 is flexible and clear. The face shield 208 can comprise an elastic band 210 fastened around the perimeter of the face shield 208. When worn by the wearer 302, the face shield 208 stretches around and contacts the perimeter of the face of the wearer 302 covering the temple vents 246, and the eyes, nose, and mouth of the wearer 302. The elastic band 210 interconnects with each of the face shield hook 224 securing the face shield 208 in position. The purified filtered air 406 emitted from the temple vents 246 inflates a region 410 between the face shield 208 and the face of the wearer 302 allowing the wearer 302 to breathe the purified filtered air 406.

In an exemplary embodiment, a separate air handler 216 can be integrated into each of the first shoulder rail end 256A and the second shoulder rail end 256B. In operation, this increases the continuous amount of purified filtered air 406 produced.

In an exemplary embodiment, the air handler 216 can be configured with removable filters 216 on each side of the blower motor 230 allowing more of the external air 402 to be drawn into the removable filters 216 in a continuous manner on either of the first shoulder rail end 256A, the second shoulder rail end 256B, or both. In this regard, either the first shoulder rail end 256A or the second shoulder rail end 256B can comprise an outer facing surface 262 and an inner facing surface 264. More than one filter port 244 can be formed on the air handler 216 to allow more than one removable filter 218 to be interconnected with each of the filter port 244 on both the outer facing surface 262 and the inner facing surface 264.

In an exemplary embodiment, the length 416 of the neck conduit 220 is adjustable to fit the neck length as well as the distance between the shoulders and the temples 304 of the wearer 302. In this regard, the neck conduit 220 can be adjusted in length to best fit the wearer 302. In some embodiments, a way to adjust the length of the neck conduit 220 can be to offer different sizes of the neck conduit 220 such as small, medium, and large. In this regard, the wearer 302 can select the length that best fits their shoulder, neck, and head anatomy. In other embodiments, a way to adjust the length of the neck conduit 220 can be to form the neck conduit 220 in more than one movable segment that allows the segments to telescope 'IN' and 'OUT' to shorten or lengthen the neck conduit 220 when the wearer 302 pulls on the ends of the neck conduit 220. In other embodiments, a way to adjust the length of the neck conduit 220 can be by allowing the first neck conduit end 294 and the first neck conduit port 292 and/or the second neck conduit end 290 and the second neck conduit port 288 to be ribbed and grooved as to allow the interconnections to click into more than one position to shorten or lengthen the distance between the shoulder rail 274 and the temple rail 222.

In an exemplary embodiment, the temple rail 222 can be formed with at least one flat surface portion 258. The flat surface portion 258 can be positioned to be in contact with the temple 304 of the wearer 302 to provide motion-free fit and stabilization of the respirator 200 when being worn by the wearer 302. In operation, the flat surface portion 258 provides a sufficiently large contacting surface that creates greater friction between the temple rail 222 and the temple 304 of the wearer 302. In addition, the force created by the temple rail 222 slightly squeezing the temple 304 of the wearer 302 is distributed across a larger surface making the respirator 200 more comfortable to wear by the wearer 302, particularly for long periods of time or in applications where the wearer 302 takes the respirator 200 'ON' and 'OFF' frequently over a long period of time, such as is common in the medical profession and other professions.

In an exemplary embodiment, at least one airflow tip 296 can be interconnected with the temple vent 246. The airflow tip redirects or otherwise positions the air flow stream of the purified filtered air 406 with respect to the eyes of the wearer 302 within the region 410 between the face shield 208 and the face of the wearer 302. In this regard, for wearers 302 that wear glasses, experience dry eyes, or for other reasons, the airflow tips 296 can redirect the stream of the purified filtered air 406 in a manner that prevents the air stream from hitting the inside of the glasses lense or otherwise directing the continuous airflow of the purified filtered air 406 too close to the eyes of the wearer 302 in an irritating manner.

In an exemplary embodiment, the respirator components including the air handler 216, removable filter 218, face shield 208, shoulder rail 274, neck conduit 220, and temple rail 222 can be fabricated from plastic, metal, polymers, rubber, glass, a fabric, combination thereof, or other suitable materials.

Referring to FIG. 13, there is illustrated one example of a method of using a neck-mount powered respirator 200. The method begins in step 1002 by way of the wearer 302 wearing respirator 200. The respirator 200 comprises at least one air handler 216. The air handler 216 comprises at least one filter port 244 and at least one blower motor 230. At least one removable filter 218 interconnects with filter port 244. A shoulder rail 274 is curvilinear and u-shaped. When worn by the wearer 302 the shoulder rail 174 fits around the back of the neck and over the shoulders of the wearer 302.

The shoulder rail 274 comprises a first shoulder rail end 256A and a second shoulder rail end 256B that when the respirator 200 is worn by the wearer 302, the first shoulder rail end 256A and the second shoulder rail end 256B are positioned proximate to the face of the wearer 302, in one of the following ways, either a midpoint 412 of the shoulder rail 274 interconnects with the air handler 216 in a manner that positions the air handler 216, when worn by the wearer 302, behind the neck of the wearer 302, and the air handler 216 comprises a first neck conduit port 292, or the shoulder rail 274 is hollow and comprises the first neck conduit port 292 and the air handler 216 is integrated into either the first shoulder rail end 256A or the second shoulder rail end 256B. The method then moves to step 1004.

In step 1004, the airflow of purified filtered air 406 is initiated through airflow channel 408. A temple rail 222 is hollow, curvilinear, u-shaped, and sized, when worn by the wearer 302, to fit snugly around the back of the head and contact the temple 304 of the wearer 302. The temple rail comprises a second neck conduit port 288, a temple vent 246 at each end of the temple rail 222, and more than one face shield hook 224 positioned on the outer surface of the temple rail 222 proximate to the temple vents 246. A neck conduit 220 is hollow and curvilinear in shape.

The neck conduit 220 comprises a first neck conduit end 294 and a second neck conduit end 290. The neck conduit 220 interconnects, in a removable manner, the first neck conduit end 294 with the first neck conduit port 292 and the second neck conduit end 290 with the second neck conduit port 288 forming a rigid structure between the shoulder rail 276, the neck conduit 220, and the temple rail 222, and forming the airflow channel 408 in one of the following ways, by ingress of an external air 402 through the removable filter 218 by way of the blower motor 230 creating a purified filtered air 406, and transport of the purified filtered air 406, inside the airflow channel 408 and without contact with the external air 402, through the air handler 216, the neck conduit 220, and the temple rail 222, and egress the purified filtered air 406 through the temple vent 246. Or, by ingress the external air 402 through the removable filter 218 by way of the blower motor 230 creating the purified filtered air 406, and transport the purified filtered air 406, inside the airflow channel 408 and without contact with the external air 402, through the air handler 216, the shoulder rail 274, the neck conduit 220, and the temple rail 222, and egress the purified filtered air 406 from the temple vent 246. The method then moves to step 1006.

In step 1006, a face shield 208 is installed. The face shield 208 is flexible and clear. The face shield 208 comprises an elastic band 210 fastened around the perimeter of the face shield 208. When worn by the wearer 302, the face shield 208 stretches around and contacts the perimeter of the face of the wearer 302 covering the temple vents 246, and the eyes, nose, and mouth of the wearer 302. The elastic band 210 interconnects with each of the face shield hook 224 securing the face shield 208 in position. The purified filtered air 406 emitted from the temple vents 246 inflates the region 410 between the face shield 208 and the face of the wearer 302 allowing the wearer 302 to breathe the purified filtered air 406. The method is the exited.

Referring to FIG. 14, there are illustrated exemplary embodiments that can be interchangeably used with the methods of the present invention.

In step 1102, by way of the wearer 1102, the length of the neck conduit 220 and the size of the temple rail 222 is selected to provide a customized comfortable fit for the wearer 302. In an exemplary embodiment, both the neck conduit 220 and the temple rail 222 can be available to wearers 302 in different sizes to accommodate different lengths of necks and head sizes. In this regard, both the neck conduit 220 and the temple rail 222 can be fabricated in small, medium, large, and other sizes, configured to be adjustable by sliding telescoping segments 'IN' and 'OUT' to change sizes, or configured to allow insertable/removable segments to be used to shorten, lengthen, and/or widen the neck conduit 220 and/or the temple rail 222 as may be required and/or desired in a particular embodiment. In operation, once appropriate size/length is established to a particular wearer, there is no need to make adjustment every time the respirator 200 is worn.

In step 1104, the respirator 200 is assembled, by way of the wearer, by interconnecting the first neck conduit end 294 with the first neck conduit port 292 and interconnecting the second neck conduit end 290 with the second neck conduit port 288.

In step 1106, the face shield 208 is coated 212 with a nanoparticle-based antimicrobial and antiviral material. In this regard, such coating 212 can kill bacteria, viruses, and other pathogens and/or microorganisms on contact further reducing the risk of the wearer 302 breathing airborne particulates, bacteria, viruses, other pathogens or microorganisms, and/or other airborne contaminants.

In step 1108, the face shield 208 can be replaced while the wearer 302 is wearing the respirator 200 and doing so without interrupting the supply of the purified filtered air 406. In this regard, in the present invention, an advantage is that the wearer can unhook and remove a used face shield 208 and install a new or different type of face shield 208 without turning the respirator 200 'OFF' or having to take off or otherwise remove the respirator 200. This saves a lot of time and allows the wearer 302 to quickly change face shields 302 such as when a face shield gets contaminated, when the wearer needs to access their face, in between patients, and in other situations.

In step 1110, the length of the neck conduit 220 is adjusted to fit the wearer. In an exemplary embodiment, the length 416 of the neck conduit 220 is adjustable to fit the neck length as well as the distance between the shoulders and the temples 304 of the wearer 302. In this regard, the neck conduit 220 can be adjusted in length to best fit the wearer 302. In some embodiments, a way to adjust the length of the neck conduit 220 can be to offer different sizes of the neck conduit 220 such as small, medium, and large. In this regard, the wearer 302 can select the length that best fits their shoulder, neck, and head anatomy. In other embodiments, a way to adjust the length of the neck conduit 220 can be to form the neck conduit 220 in more than one movable segment that allows the segments to telescope 'IN' and 'OUT' to shorten or lengthen the neck conduit 220 when the wearer 302 pulls on the ends of the neck conduit 220. In other embodiments, a way to adjust the length of the neck conduit 220 can be by allowing the first neck conduit end 294 and the first neck conduit port 292 and/or the second neck conduit end 290 and the second neck conduit port 288 to be ribbed and grooved as to allow the interconnections to click into more than one position to shorten or lengthen the distance between the shoulder rail 274 and the temple rail 222.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A neck-mount powered respirator comprising:
at least one of an air handler comprises a first neck conduit port, a filter port, and a blower motor;
at least one of a removable filter interconnects with the filter port;
a shoulder rail is curvilinear and u-shaped, when worn by a wearer, the shoulder rail fits around the back of the neck and over the shoulders of the wearer, the shoulder rail comprises a first shoulder rail end and a second shoulder rail end that, when worn by the wearer, are positioned proximate to the face of the wearer, a midpoint of the shoulder rail interconnects with the air handler in a manner that positions the air handler, when worn by the wearer, behind the neck of the wearer;
a temple rail is hollow, curvilinear, u-shaped, and sized, when worn by the wearer, to fit snugly around the back of the head and contact the temple of the wearer, the temple rail comprises a second neck conduit port, a temple vent at each end of the temple rail, and more than one of a face shield hook positioned on an outer surface of the temple rail proximate to the temple vent;
a neck conduit is hollow and curvilinear in shape, the neck conduit comprises a first neck conduit end and a second neck conduit end, the neck conduit interconnects, in a removable manner, the first neck conduit end with the first neck conduit port and the second neck conduit end with the second neck conduit port forming a rigid structure among the shoulder rail, the neck conduit, and the temple rail, and forming an airflow channel which ingresses an external air through the removable filter by way of the blower motor creating a purified filtered air, and transports the purified filtered air, inside the airflow channel and without contact with the external air, through the air handler, the neck conduit, and the temple rail, and egresses the purified filtered air from the temple vent; and
a face shield is flexible and clear, the face shield comprises an elastic band fastened around the perimeter of the face shield, when worn by the wearer, the face shield stretches around and contacts the perimeter of the face of the wearer covering the temple vents, and the eyes, nose, and mouth of the wearer, the elastic band interconnects with each of the face shield hooks, securing the face shield in position, the purified filtered air emitted from the temple vents inflates the region between the face shield and the face of the wearer allowing the wearer to breathe the purified filtered air.

2. The neck-mount powered respirator in accordance with claim 1, wherein the first shoulder rail end or the second shoulder rail end comprises a compartment for storing a power source.

3. The neck-mount powered respirator in accordance with claim 1, further comprising:
a respirator control system that comprises a power source, the blower motor, and a switch or speed control.

4. The neck-mount powered respirator in accordance with claim 3, wherein the switch or the speed control is accessible to the wearer proximate to the first shoulder rail end or the second shoulder rail end.

5. The neck-mount powered respirator in accordance with claim 1, further comprising:
at least one of an airflow tip is interconnected with the temple vent, the airflow tip is configured to position an air flow stream of the purified filtered air with respect to the eyes of the wearer within the region between the face shield and the face of the wearer.

6. The neck-mount powered respirator in accordance with claim 1, wherein the removable filter comprises at least one filter material, at least one filter screen, and a filter enclosure, the filter material and the filter screen are enclosed within the filter enclosure, the filter enclosure is configured to insert and rotate to removably fasten within the filter port.

7. The neck-mount powered respirator in accordance with claim 1, wherein a length of the neck conduit is adjustable to fit the wearer.

8. The neck-mount powered respirator in accordance with claim 1, wherein the face shield is coated with a nanoparticle-based antimicrobial and antiviral material.

9. The neck-mount powered respirator in accordance with claim 1, wherein the temple rail is formed with at least one of a flat surface portion, the flat surface portion is configured to be in contact with the temple of the wearer to provide fit stabilization of the respirator when being worn by the wearer.

10. A neck-mount powered respirator comprising:
at least one of an air handler comprises at least one of a filter port, and at least one of a blower motor;
at least one of a removable filter interconnects with the filter port;
a shoulder rail is hollow, curvilinear, and u-shaped, when worn by a wearer, the shoulder rail fits around the back of the neck and over the shoulders of the wearer, the shoulder rail comprises a first neck conduit port, a first shoulder rail end, and a second shoulder rail end, when worn by the wearer, the first neck conduit port is positioned proximate to the back of the neck of the wearer, and the first shoulder rail and the second shoulder rail are positioned proximate to the face of the wearer, the air handler is integrated into either the first shoulder rail end or the second shoulder rail end;
a temple rail is hollow, curvilinear, u-shaped, and sized, when worn by the wearer, to fit snugly around the back of the head and contact the temple of the wearer, the temple rail comprises a second neck conduit port, a temple vent at each end of the temple rail, and more than one of a face shield hook positioned on outer surface of the temple rail proximate to the temple vent;
a neck conduit is hollow and curvilinear in shape, the neck conduit comprises a first neck conduit end and a second neck conduit end, the neck conduit interconnects, in a removable manner, the first neck conduit end with the first neck conduit port and the second neck conduit end with the second neck conduit port forming a rigid structure among the shoulder rail, the neck conduit, and the temple rail, and forming an airflow channel which ingresses an external air through the removable filter by way of the blower motor creating a purified filtered air, and transports the purified filtered air, inside the airflow channel and without contact with the external air, through the air handler, the shoulder rail, the neck conduit, and the temple rail, and egresses the purified filtered air from the temple vent; and a face shield is flexible and clear, the face shield comprises an elastic band fastened around the perimeter of the face shield, when worn by the wearer, the face shield stretches around and contacts the perimeter of the face of the wearer covering the temple vents, and the eyes, nose, and mouth of the wearer, the elastic band interconnects with each of the face shield hooks, securing the face shield in position, the purified filtered air emitted from the temple vent inflates a region between the face shield and the face of the wearer allowing the wearer to breathe the purified filtered air.

11. The neck-mounted respirator in accordance with claim 10, wherein the at least one of the air handler further comprises a first air handler and a second air handler, the first air handler is integrated into the first shoulder rail end and the second air handler is integrated into the second shoulder rail end.

12. The neck-mount powered respirator in accordance with claim 11, wherein each of the first shoulder rail end and the second shoulder rail end comprises an outer facing surface and an inner facing surface, each of the first air handler and the second air handler comprises more than one of the filter ports formed on the outer facing surface and the inner facing surface of the respective shoulder rail end, and more than one of the removable filters is interconnected with the filter ports of each of the first air handler and the second air handler.

13. The neck-mount powered respirator in accordance with claim 10, wherein a length of the neck conduit is adjustable to fit the wearer.

14. The neck-mount powered respirator in accordance with claim 10, wherein the temple rail is formed with at least one of a flat surface portion, the flat surface portion is configured to be in contact with the temple of the wearer to provide fit stabilization of the respirator when being worn by the wearer.

15. The neck-mount powered respirator in accordance with claim 10, further comprising:

at least one of an airflow tip is interconnected with the temple vent, the airflow tip is configured to position an air flow stream of the purified filtered air with respect to the eyes of the wearer within the region between the face shield and the face of the wearer.

16. A method of using a neck-mount powered respirator comprising the steps of:

wearing, by way of a wearer, a respirator, the respirator comprises at least one of an air handler, the air handler comprises at least one of a filter port and at least one of a blower motor, at least one of a removable filter interconnects with the filter port, a shoulder rail is curvilinear and u-shaped, wherein, when worn by the wearer, the shoulder rail fits around the back of the neck and over the shoulders of the wearer, the shoulder rail comprises a first shoulder rail end and a second shoulder rail end that, when worn by the wearer, are positioned proximate to the face of the wearer, wherein the respirator is configured in one of the following two arrangements:

(a) a midpoint of the shoulder rail interconnects with the air handler in a manner that positions the air handler, when worn by the wearer, behind the neck of the wearer, the air handler comprises a first neck conduit port, and an airflow channel is formed that transports a purified filtered air, inside the airflow channel and without contact with a external air, through the air handler, the neck conduit, and the temple rail; or (b) the shoulder rail is hollow and comprises the first neck conduit port, the air handler is integrated into either the first shoulder rail end or the second shoulder rail end, and the airflow channel is formed that transports the purified filtered air, inside the airflow channel and without contact with the external air, through the air handler, the shoulder rail, the neck conduit, and the temple rail;

initiating an airflow of the purified filtered air through the airflow channel, a temple rail is hollow, curvilinear, u-shaped, and sized, when worn by the wearer, to fit snugly around the back of the head and contact the temple of the wearer, the temple rail comprises a second neck conduit port, a temple vent at each end of the temple rail, and more than one of a face shield hook positioned on an outer surface of the temple rail proximate to the temple vent, a neck conduit is hollow and curvilinear in shape, the neck conduit comprises a first neck conduit end and a second neck conduit end, the neck conduit interconnects, in a removable manner, the first neck conduit end with the first neck conduit port and the second neck conduit end with the second neck conduit port, forming a rigid structure among the shoulder rail, the neck conduit, and the temple rail, wherein the external air is ingressed through the removable filter by way of the blower motor to create the purified filtered air, and the purified filtered air egresses from the temple vent; and installing a face shield, the face shield is flexible and clear, the face shield comprises an elastic band fastened around the perimeter of the face shield, when worn by the wearer, the face shield stretches around and contacts the perimeter of the face of the wearer covering the temple vents, and the eyes, nose, and mouth of the wearer, the elastic band interconnects with each of the face shield hooks, securing the face shield in position, the purified filtered air emitted from the temple vent inflates the region between the face shield and the face of the wearer, allowing the wearer to breathe the purified filtered air.

17. The method of using the respirator in accordance with claim 16, further comprising the step of:

selecting, by way of the wearer, a length of the neck conduit and size of the temple rail to provide a customized comfortable fit for the wearer.

18. The method of using the respirator in accordance with claim 16, further comprising the step of:

assembling the respirator, by way of the wearer, by interconnecting the first neck conduit end with the first neck conduit port and interconnecting the second neck conduit end with the second neck conduit port.

19. The method of using the respirator in accordance with claim 16, further comprising the step of:

replacing the face shield while the wearer is wearing the respirator without interrupting a supply of the purified filtered air.

20. The method of using the respirator in accordance with claim 16, further comprising the step of:

adjusting a length of the neck conduit to fit the wearer.

\* \* \* \* \*